US012648756B2

(12) United States Patent
De Lange

(10) Patent No.: US 12,648,756 B2
(45) Date of Patent: Jun. 9, 2026

(54) METHOD FOR GENERATING AN ULTRASOUND IMAGE BASED ON A DISPLACEMENT DETERMINATION IN A REFERENCE IMAGE

(71) Applicant: KONINKLIJKE PHILIPS N.V., Eindhoven (NL)

(72) Inventor: Alphonsus Anthonius Jozef De Lange, Overpelt (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 18/024,649

(22) PCT Filed: Sep. 1, 2021

(86) PCT No.: PCT/EP2021/074097
§ 371 (c)(1),
(2) Date: Mar. 3, 2023

(87) PCT Pub. No.: WO2022/053365
PCT Pub. Date: Mar. 17, 2022

(65) Prior Publication Data
US 2024/0023931 A1     Jan. 25, 2024

(30) Foreign Application Priority Data
Sep. 10, 2020     (EP) ..................................... 20195542

(51) Int. Cl.
*A61B 8/00*          (2006.01)
*G06T 7/00*          (2017.01)
(52) U.S. Cl.
CPC .......... *A61B 8/4416* (2013.01); *G06T 7/0012* (2013.01); *G06T 2207/10132* (2013.01)
(58) Field of Classification Search
CPC .............................. G01R 33/4814; G06T 7/30
See application file for complete search history.

(56) References Cited

U.S. PATENT DOCUMENTS

2018/0235701 A1     8/2018   Gerard et al.
2020/0060512 A1     2/2020   Holsing et al.
(Continued)

FOREIGN PATENT DOCUMENTS

WO          2005111932 A1     11/2005
WO          2008081396 A1      7/2008
(Continued)

OTHER PUBLICATIONS

Gobbi et al., "Ultrasound/MRI Overlay with Image Warping for Neurosurgery," (Oct. 2000), Lecture Notes in Computer Science 1935:106-114. (Year: 2000).*
(Continued)

*Primary Examiner* — Keith M Raymond
*Assistant Examiner* — Ashish S. Jasani

(57)          ABSTRACT
A method provides a source of secondary imaging of an anatomical region of interest for use during a medical procedure. The method is based on acquiring in advance a set of reference images in a secondary imaging modality of the anatomical region over the course of movement of an object or body within the region. Different movement positions of the object within the reference images are indexed via measurement of displacement of a pre-defined reference point fixed relative to the anatomy of interest. This is measured using an ultrasound imaging probe which images the anatomical region simultaneously with the secondary imaging modality. The detected reference point position for each reference image is recorded along with each image frame. During the intervention, an ultrasound image probe is again used, preferably set up in the same position relative to the anatomy, and captures images of the same anatomy during the procedure. The reference images can be recalled in real time based on measuring the reference point displacement using the ultrasound images and querying the
(Continued)

dataset for the relevant associated image. This can be displayed alongside, or in place of, each ultrasound image frame.

11 Claims, 7 Drawing Sheets

(56)                    References Cited

U.S. PATENT DOCUMENTS

| | | |
|---|---|---|
| 2020/0146635 A1 | 5/2020 | Wang et al. |
| 2020/0273184 A1 | 8/2020 | Dufor et al. |

FOREIGN PATENT DOCUMENTS

| | | |
|---|---|---|
| WO | 2015086848 A1 | 6/2015 |
| WO | 2018206473 A1 | 11/2018 |
| WO | 2019110115 A1 | 6/2019 |
| WO | 2019219861 A1 | 11/2019 |

OTHER PUBLICATIONS

International Search Report and Written Opinion for PCT/EP2021/074097; Mailing date: Nov. 19, 2021, 9 pages.

Hewitt, J., "Philips transforms image-guided therapy with global launch of Azurion Platform", Medical Xpress, 2017, 5 pages.

Haan, G. De et al., "An efficient true-motion estimator using candidate vectors from a parametric motion model", IEEE Transactions on Circuits and Systems for Video Technology, 1998, vol. 8, No. 1, pp. 85-91.

Yoshikawa, H. et al., "Ultrasound Sub-pixel Motion-tracking Method with Out-of-plane Motion Detection for Precise Vascular Imaging", Ultrasound in Medicine & Biology, 2020, vol. 46, Issue 3, pp. 782-795.

Zachiu, C. et al., "An improved optical flow tracking technique for real-time MR-guided beam therapies in moving organs", IEEE International Symposium on Biomedical Imaging (ISBI 2016), 2016, 2 pages.

* cited by examiner

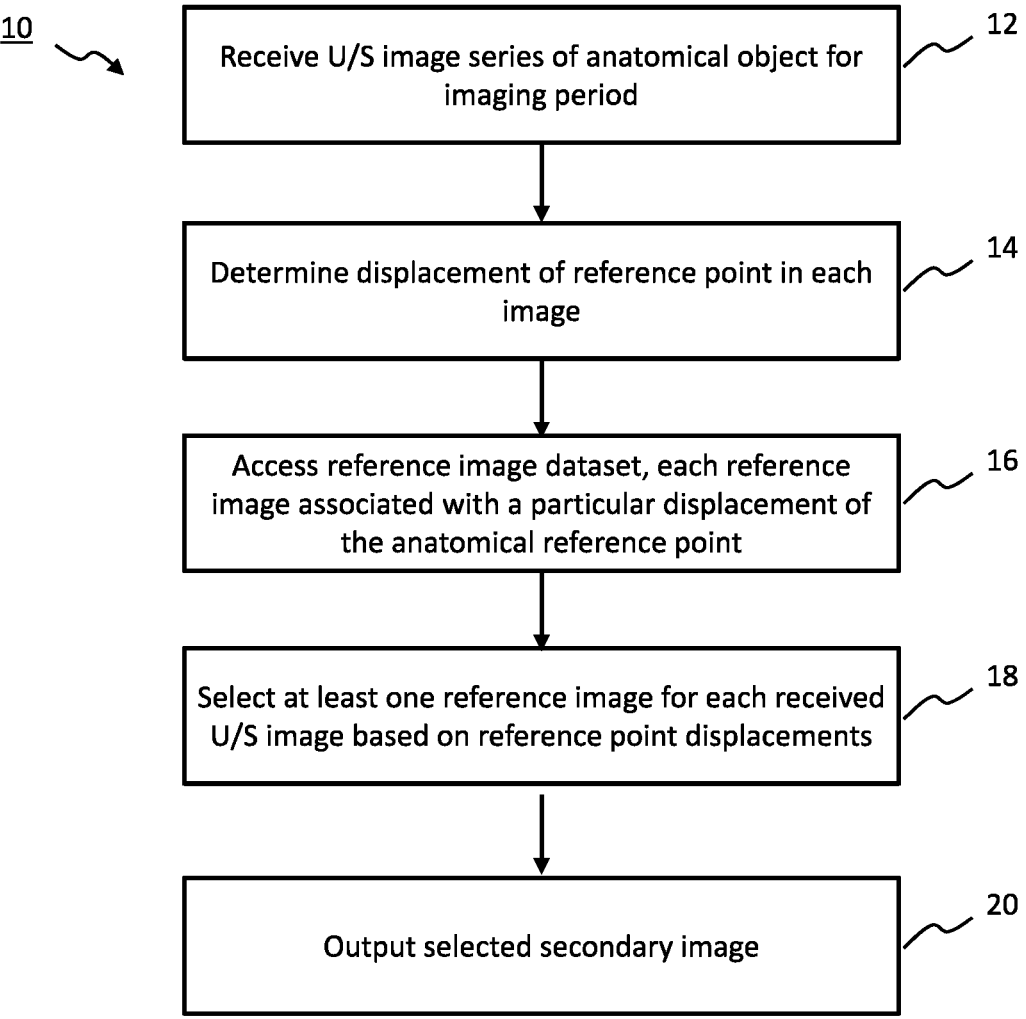

10

Receive U/S image series of anatomical object for imaging period          12

Determine displacement of reference point in each image          14

Access reference image dataset, each reference image associated with a particular displacement of the anatomical reference point          16

Select at least one reference image for each received U/S image based on reference point displacements          18

Output selected secondary image          20

FIG. 1

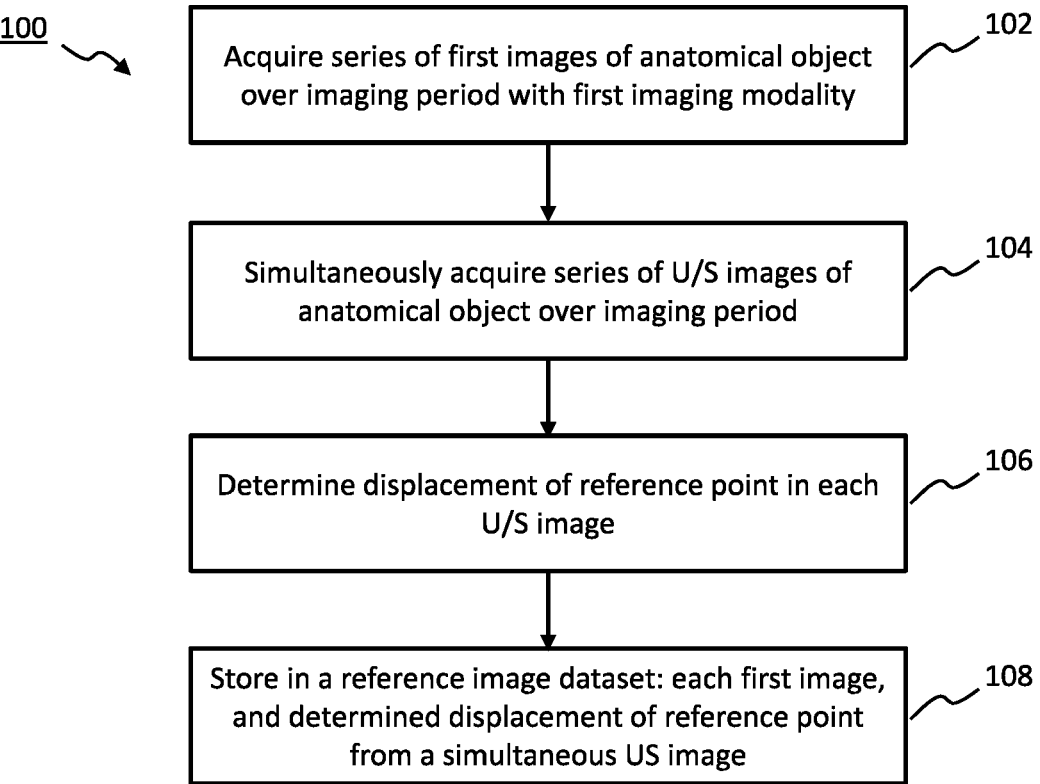

100

Acquire series of first images of anatomical object over imaging period with first imaging modality    102

Simultaneously acquire series of U/S images of anatomical object over imaging period    104

Determine displacement of reference point in each U/S image    106

Store in a reference image dataset: each first image, and determined displacement of reference point from a simultaneous US image    108

METHOD FOR GENERATING AN ULTRASOUND IMAGE BASED ON A DISPLACEMENT DETERMINATION IN A REFERENCE IMAGE

CROSS-REFERENCE TO PRIOR APPLICATIONS

This application is the U.S. National Phase application under 35 U.S.C. § 371 of International Application No. PCT/EP2021/074097, filed on Sep. 1, 2021, which claims the benefit of European Patent Application No. 20195542.4, filed on Sep. 10, 2020. These applications are hereby incorporated by reference herein.

FIELD OF THE INVENTION

This invention relates to a method for providing a source of secondary medical imaging of an anatomy, in particular for use during a medical procedure.

BACKGROUND OF THE INVENTION

Medical imaging can be performed during a medical procedure to provide visual guidance to a clinician. For example, it can be performed during an interventional procedure to provide visualization of the anatomy which is the subject of the intervention, for example a region containing a lesion or tumor (or other object of interest).

The medical imaging can be provided live in real time. Ideally, the imaging provides both high spatial and temporal resolution. This is particularly important in the case of imaging anatomical areas which are subject to movement within the body due to natural movement actions or cycles, e.g. movement of the lungs, liver, or the heart. Here, the anatomy subject to intervention may move continuously and thus high temporal resolution imaging is desirable.

High spatial resolution provides a higher level of spatial detail. This is particularly important for interventions which require precision interaction with the anatomical feature.

Sufficiently high spatial resolution can be obtained with imaging modalities such as MRI, CT and Fluoroscopy C-Arm equipment. However, MRI and CT scanners pose problems for real-time imaging due to the size of the equipment and limited accessibility to the patient to perform the interventional procedure. C-Arm fluoroscopy has the disadvantage that it emits harmful radiation and thus is not ideal as a choice for continuous imaging during a relatively long procedure.

By contrast, ultrasound imaging is compact, non-ionizing and has higher temporal resolution. However, spatial resolution of ultrasound images is considerably lower.

Thus an imaging approach able to provide both high spatial and temporal resolution imaging of a region of interest, while being compact and non-ionizing would be desirable.

Multimodality imaging is a further example approach to providing live imaging during a procedure. This comprises a combination of imaging modalities. Examples include combined PET and CT scans for accurate localization of tumors. However this remains subject to the same disadvantages as CT alone, with respect to large apparatus size.

A further example comprises combining live Fluoroscopy (C-Arm equipment) with annotated prior CT scans to localize and treat regions of interest.

However, registration of live images and prior CT or MRI scan imaging is complex and computationally demanding. It is also often inaccurate, due to the complex image processing algorithms that must be applied, which may provide erroneous registration. It is also typically based on rigid body structures, such as the vertebra column to provide landmarks for registration. Thus, for purely soft body structures, it is less useful. Furthermore, live registration of moving structures based on pre-recorded image data and live data is even more complex.

Thus, there remains a need for an imaging approach able to provide both high spatial and temporal resolution imaging of a region of interest, while being compact and non-ionizing, and which does not require complex real-time image registration procedures.

SUMMARY OF THE INVENTION

The invention is defined by the claims.

According to examples in accordance with an aspect of the invention, there is provided a method of providing a source of secondary imaging of a moving anatomical object of interest of a patient the method comprising:

receiving a series of ultrasound images representative of an area containing the anatomical object, the images corresponding to different time points over an imaging period;

determining for each ultrasound image a displacement within a frame of reference fixed with respect to the ultrasound imaging field of view, of a pre-defined reference point, fixed with respect to the anatomical object accessing a dataset comprising a set of reference images representative of the anatomical object in different movement positions, the reference images being corresponding to a different imaging modality to the ultrasound images, and wherein each reference image is associated in the dataset with a corresponding recorded displacement of said reference point on the object within a frame of reference fixed with respect to the reference imaging field of view;

selecting, for each received ultrasound image at least one of the reference images based on the determined displacement of the reference point in the received image; and generating for each received ultrasound image an output representative of the selected reference image, the output providing a source of secondary imaging.

The reference images are preferably of higher spatial resolution than the received ultrasound images.

The approach according to embodiments of the present invention, is to pre-acquire in advance a set of images of the anatomical object using a secondary (preferably higher spatial resolution) imaging modality over a time window, over the course of movement of the object. Simultaneously with the high quality imaging acquisition, ultrasound images are also acquired of the same anatomical region, and a displacement of a reference point having a fixed location relative the imaged anatomy is tracked within the ultrasound images. For each acquired high resolution image, the displacement of the reference point in the ultrasound images is recorded to thereby form a dataset comprising the high resolution images of the anatomical object in different movement positions, and each image associated with a displacement of the reference point in the ultrasound images.

The above represents a set-up or calibration or acquisition phase.

Subsequently, during a retrieval phase (for example during an interventional procedure), the high resolution imaging modality is not operated continuously. Instead, ultrasound images are continuously or recurrently acquired, and for each acquired image, the displacement of the reference point is identified, and the associated high resolution reference image retrieved from the dataset and displayed to the clinician.

This approach avoids the need for real time registration between the real-time ultrasound imaging and the stored reference images. Instead, the registration between the two is achieved indirectly via use of the reference point displacement. A spatially registered secondary image can be identified based on the single measured variable of the reference point displacement.

The ultrasound probe during the retrieval phase may be configured in the same physical pose (position and orientation) relative to the patient anatomy as during the acquisition phase, or there may be a known mapping between the field of view frame of reference of the probe during the retrieval phase and the field of view frame of reference during the set-up phase. In this way, the measured displacement of the reference point in the ultrasound images acquired in the recall phase will be in registration with the recorded displacements for the reference images.

The 'frame of reference fixed with respect to the reference imaging field of view' referred to above may be the same as the 'frame of reference fixed with respect to the ultrasound imaging field of view'. It may be defined by a co-ordinate system which is the same as a co-ordinate system of the ultrasound imaging field of view, or may be defined by a co-ordinate system which is different but has a known mapping or registration with the ultrasound imaging co-ordinate system.

It is noted that although a reference point is referred to, this can mean a single point or a line, e.g. an edge of an anatomical structure such as an organ, or an area or a volume. Thus, reference throughout this disclosure to a reference point should be understood as reference to any of a point, line, area or volume.

The ultrasound imaging can be 2D or 3D ultrasound imaging. The secondary imaging modality can be 2D or 3D.

The method may further comprise displaying each selected reference image on a display device. The method may optionally comprise displaying each selected reference image concurrently with the corresponding received ultrasound image.

If the method is performed in real time during an interventional procedure, this allows the clinician to derive the benefit of both real-time live imaging of the anatomical area (from ultrasound images) as well as the (preferably higher spatial resolution) pre-acquired images of the area.

In accordance with one or more embodiments, the ultrasound images may be received in real time during an interventional procedure. For example, the images may be received from an ultrasound imaging transducer unit (e.g. probe), or an ultrasound imaging apparatus to which is coupled an ultrasound transducer unit.

The anatomical object may be a cyclically moving anatomical object. The imaging period may correspond to one or more movement cycles of the anatomical object.

The stored dataset may comprise a set of said reference images corresponding to a series of time points which span a complete movement cycle of the anatomical object.

Thus, in this set of embodiments, the reference dataset effectively forms a calibrated sequence of reference images of a complete movement cycle of the anatomical object.

As discussed, the reference images of the dataset may be images previously acquired for the same anatomical object during a calibration or acquisition phase, and wherein the associated displacement of the reference point for each reference image is a displacement recorded in a simultaneously acquired ultrasound image relative to a frame of reference fixed with respect to the ultrasound imaging field of view.

The frame of reference used to record the displacement in the calibration phase may be the same as the frame of reference of the ultrasound imaging field of view used in the retrieval phase. The ultrasound imaging field of view may have a co-ordinate system associated with it. The determined displacement of the reference point in each received ultrasound image may be represented in terms of this co-ordinate system. The recorded reference point displacement for each of the reference images in the dataset may also be recorded in terms of the same co-ordinate system, thus enabling easy lookup of the corresponding reference image for a given measured displacement of the reference point during the retrieval phase.

Alternatively, there may be applied a mapping or transformation between the ultrasound field of view co-ordinate systems in the calibration and retrieval phases.

The ultrasound images may be received from an ultrasound imaging apparatus which comprises an ultrasound transducer unit (e.g. probe) in a fixed pose relative to the patient anatomy. The ultrasound transducer unit may be held by a support frame permitting adjustment and releasable fixing of a pose of the probe.

In some embodiments, the support frame may be adapted to generate a data output comprising a pose indicator indicative of a current pose position of the frame (or of the probe held within the frame). This allows for example the-co-ordinate system of the ultrasound imaging probe to be precisely tracked and controlled, allowing for registration to be performed (if necessary) between the recorded reference point displacements in the reference dataset and the measured displacements during the retrieval phase. Alternatively, it can be used to ensure that the ultrasound field of view in each of the calibration phase and retrieval phase match. It can also be used for registering the co-ordinate systems of the ultrasound imaging and the secondary imaging modality in some examples.

In accordance with one or more embodiments, the method may further comprise generating an interpolated reference image responsive to detecting that the determined displacement of the reference point in a received image does not match the recorded reference point displacement of any of the reference images in the dataset and is intermediate the recorded reference point displacements of a first and second of the reference images. The interpolated reference image may be generated in this case based on interpolation between said first and second of the reference images.

This provides the technical benefit of further increasing the temporal resolution of the secondary imaging source, since a secondary image can be output at every possible movement position of the anatomy, even if the dataset is missing a pre-stored image corresponding to a particular movement position.

A further aspect of the invention provides a method of performing the calibration or acquisition phase discussed above.

In particular, a further aspect of the invention provides a method of generating a dataset of reference images of a moving anatomical object for use in providing a source of secondary imaging. The method comprises acquiring, using a first imaging modality a series of first images of an anatomical region containing the anatomical object over an imaging period. The method further comprises, simultaneously with the acquiring of the series of first images, acquiring a series of ultrasound images of a region containing the same anatomical object over said imaging period, wherein the first imaging modality is different to that of the ultrasound images. The method further comprises, for each of the ultrasound images, determining a displacement, within a frame of reference fixed with respect to the ultrasound imaging field of view, of a pre-defined reference point fixed relative to the anatomical object. The method further comprises, for each of the first images, storing in a dataset a representation of the first image and an associated record of the determined displacement of the reference point within one of the ultrasound images acquired simultaneously with the first image, to thereby generate a reference imaging dataset for providing a source of secondary imaging.

This method thus defines the calibration or set-up phase in which the dataset of reference images is acquired. The 'first images' in this method correspond to the reference images of the retrieval phase defined previously.

The method may further comprise a step of registering a co-ordinate system of the ultrasound imaging frame of reference with a co-ordinate system of the secondary imaging modality frame of reference. Registration in this context means that both ultrasound and secondary images are put in the same geometrical frame of reference (coordinate system). This may be useful for visualization purposes, so that the ultrasound images and reference images correspond to the same area of the anatomy. For example, this means that both image sets could be viewed together according to certain embodiments, at the same size, orientation, spatial location and may even be visually superimposed (fused).

In accordance with one or more embodiments, the anatomical object being imaged may be a cyclically moving anatomical object and wherein the imaging period corresponds to one or more movement cycles of the anatomical object. For example, the stored dataset of the first images (reference images) may comprise a set of said first images corresponding to a series of time points which span a complete movement cycle of the anatomical object.

The method may comprise acquiring the image data over a plurality of movement cycles of the anatomical object, and generating an average or aggregate dataset for a single movement cycle based on the image data from the plurality of movement cycles. For example in each movement cycle, the secondary imaging modality may capture image frames corresponding to slightly different time points or phases in the cycle compared to the previously imaged cycles. Thus, over a set of multiple cycles, a more comprehensive secondary image dataset (more time points) can be compiled.

According to one or more embodiments, the method of the invention may comprise performing the calibration or set-up phase, in accordance with any example or embodiment outlined above or described below, or in accordance with any claim of this application, and may further comprise performing the retrieval phase, subsequent to the calibration phase. The retrieval phase may be in accordance with any example or embodiment outlined above or described below, or in accordance with any claim of this application. The reference imaging dataset generated in the calibration or set-up phase is used as the dataset of reference images in the retrieval phase.

For instance, in advantageous examples, both phases are performed during the same single interventional procedure.

Examples in accordance with a further aspect of the invention provide a processing arrangement arranged to provide a source of secondary imaging of a moving anatomical object of interest of a patient. The processing arrangement is adapted to receive a series of ultrasound images representative of an area containing the anatomical object, the images corresponding to different time points over an imaging period. The processing arrangement is further adapted to determine for each ultrasound image a displacement within a frame of reference fixed with respect to the ultrasound imaging field of view, of a pre-defined reference point fixed relative to the anatomical object. The processing arrangement is further adapted to access a dataset comprising a set of reference images representative of the anatomical object in different movement positions, the reference images being of a different imaging modality to the ultrasound images, and wherein each reference image is associated in the dataset with a corresponding recorded displacement of said reference point on the object within a frame of reference fixed with respect to the reference imaging field of view. The processing arrangement is further adapted to select, for each received ultrasound image, at least one of the reference images based on the determined displacement of the reference point in the received image. The processing arrangement is further adapted to generate for each received ultrasound image an output representative of the selected reference image, the output providing a source of secondary imaging.

In other words, the processing arrangement is adapted to perform the retrieval phase of the secondary imaging method, in accordance with any example or embodiment outlined above or described below, or in accordance with any claim of this application.

Optionally, the processing arrangement may further comprise a datastore storing said dataset of reference images. Alternatively, the datastore may be external to the processing arrangement. The processing arrangement may include one or more processing modules which perform the processing functions, and wherein the one or more processing modules include an input/output for communicating with the datastore to access the dataset.

A further aspect of the invention may provide a processing arrangement which is adapted to perform the set-up or calibration phase of the method, as set out in accordance with any example or embodiment outlined above or described below, or in accordance with any claim of this application.

A processing arrangement may be provided which is adapted to perform both of the phases of the method: first the set-up phase, then the retrieval phase. The processing arrangement may be adapted to perform the set-up phase responsive to receipt of an input trigger signal, which may for example be received from a user interface (e.g. the clinician triggers execution or re-execution of the set-up phase at selected moments during an interventional procedure).

Examples in accordance with a further aspect of the invention provide a system. The system comprises a processing arrangement in accordance with any example or embodiment outlined above or described below, or in accordance with any claim of this application. The system further comprises an ultrasound imaging apparatus comprising an ultrasound transducer unit the imaging apparatus for acquiring the ultrasound images of the anatomical body, and arranged to communicate the acquired ultrasound images to the control unit. The ultrasound transducer unit may be an ultrasound probe for example.

The system may further comprise a support frame arranged to hold the ultrasound transducer unit releasably fixed in an adjustable pose relative to the patient anatomy. The support frame may be adapted to generate a data output comprising a pose indicator indicative of a current pose position of the frame.

This allows for example the-co-ordinate system of the ultrasound imaging probe to be precisely tracked and controlled, allowing for registration to be performed between the recorded anatomical displacements in the reference dataset and the measured displacements during the recall phase.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1 shows steps of an example method according to one or more embodiments of a first aspect of the invention;

FIG. 4 shows steps of an example method according to one or more embodiments of a second aspect of the invention;

DETAILED DESCRIPTION OF THE EMBODIMENTS

Figures 2, 3:
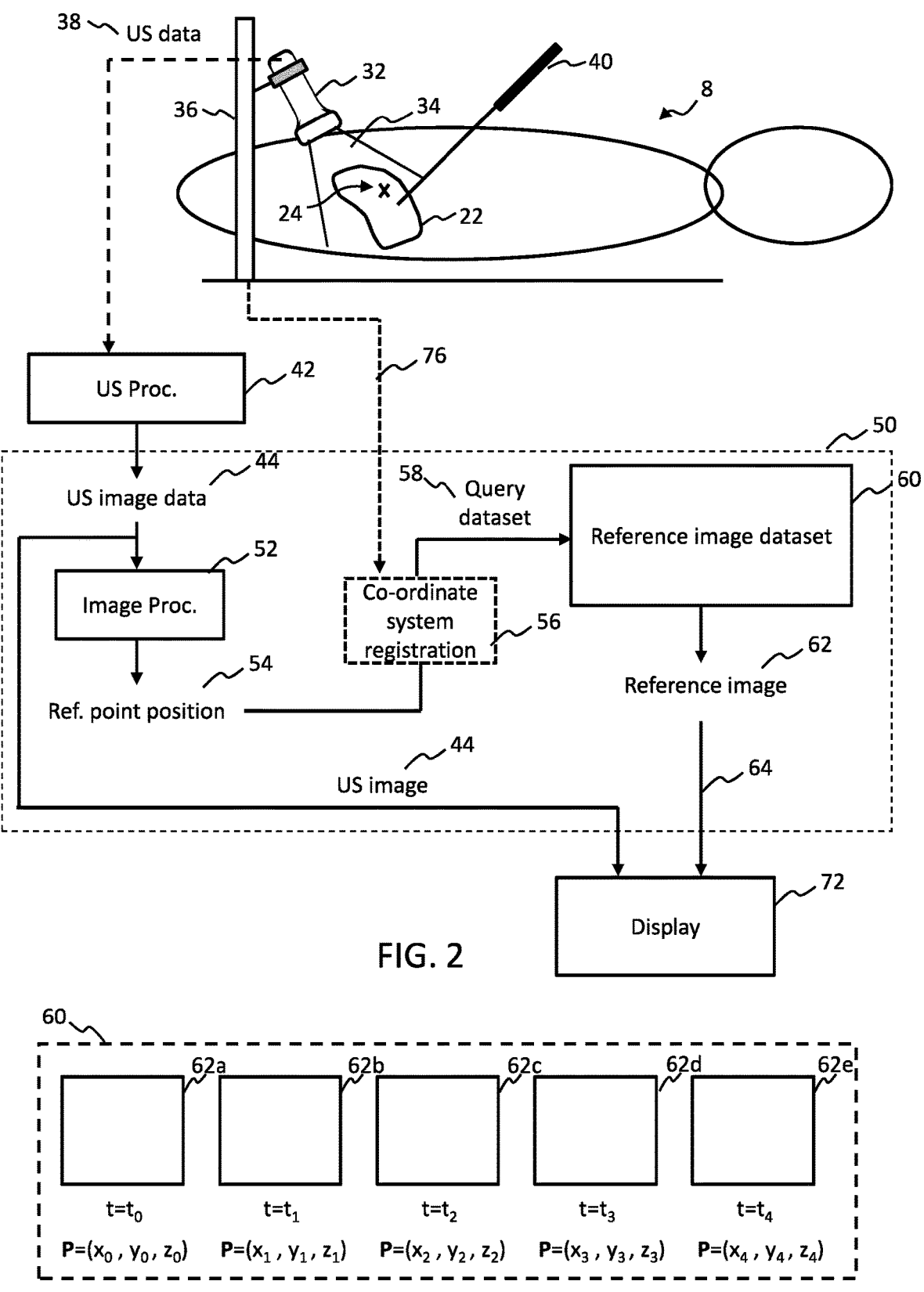
FIG. 2 illustrates an example workflow according to one or more embodiments of the invention.
FIG. 3 schematically illustrates an example reference imaging dataset.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for providing a source of secondary imaging of an anatomical region of interest for use during a medical procedure. The method is based on acquiring in advance a set of reference images in a secondary imaging modality of the anatomical region over the course of movement of an object or body within the region. Different movement positions of the object within the reference images are indexed via measurement of displacement of a pre-defined reference point fixed relative to the anatomy of interest. This is measured using an ultrasound imaging probe which images the anatomical region simultaneously with the secondary imaging modality. The detected reference point position for each reference image is recorded along with each image frame. During the intervention, an ultrasound image probe is again used, preferably set up in the same position relative to the anatomy, and captures images of the same anatomy during the procedure. The reference images can be recalled in real time based on measuring the reference point displacement using the ultrasound images and querying the dataset for the relevant associated image. This can be displayed alongside, or in place of, each ultrasound image frame.

The overall approach can be divided into two main phases: a set-up or calibration phase, in which the reference image dataset is acquired, and a recall or retrieval phase in which the reference images are retrieved based on real time ultrasound measurement of position of the anatomy.

FIG. 1 outlines, in block diagram form, the basic steps of a method according to a first aspect of the invention, for performing the retrieval phase. The steps will first be outlined in summary, before each being described in more depth, with reference to an exemplary workflow shown in FIG. 2.

The method is for providing a source of secondary imaging of a moving anatomical object 22 of interest of a patient 8.

The method comprises receiving 12 a series of ultrasound images 44 representative of an area containing the anatomical object, the images corresponding to different time points over an imaging period.

The method further comprises determining 14 for each ultrasound image a displacement 54, within a frame of reference fixed with respect to the ultrasound imaging field of view, of a pre-defined reference point 24 on the anatomical object 22, or at a location fixed relative to the anatomical object.

The method further comprises accessing 16 a dataset 60 comprising a set of reference images 62 representative of the anatomical object in different movement positions, the reference images corresponding to images captured using a different imaging modality to the ultrasound images. Each reference image is associated in the dataset with a corresponding recorded displacement of the reference point on the object within a frame of reference fixed with respect to the reference imaging field of view.

The method further comprises selecting 18, for each received ultrasound image 44, at least one of the reference images 62 based on the determined displacement of the reference point in the received image. The method further comprises generating 20 for each received ultrasound image an output 64 representative of the selected reference image, the output providing a source of secondary imaging.

FIG. 2 schematically illustrates in more detail an example workflow of the method according to one or more embodiments. Exemplary components of a system which may be used to implement the method are also schematically illustrated.

The method 10 may advantageously be performed in real time during a medical procedure, for example an interventional medical procedure. Non-limiting examples in include minimally invasive image guided interventional procedures, such as for instance taking biopsies of organs in the abdomen. FIG. 2 depicts a patient 8 during an interventional procedure, wherein a surgical tool 40 is inserted in the body of the subject. The procedure relates to an anatomical object of interest 22. Non-limiting examples include the liver, lungs, kidney, stomach, heart or any other organ or internal structure.

During the course of the procedure, real time ultrasound imaging is performed using an ultrasound imaging apparatus which comprises an ultrasound transducer unit, in this example taking the form of an ultrasound probe. The ultrasound transducer unit 32 is held in a fixed pose relative to the patient anatomy. The pose defines the position and orientation of the probe, for example relative to the patient anatomy. The ultrasound transducer unit 32 has an imaging field of view 34. The field of view covers an anatomical area within the patient 8 which includes the object of interest 22. The field of view also covers a fixed reference point 24 on the object of interest, or at an anatomical point which is fixed relative to the object of interest. The reference point should be physically coupled to the object in the sense that it follows or mirrors any movement of the object of interest, such that it can be used as a landmark to track movement of the object.

Optionally, the ultrasound transducer unit is held by a support frame 36 permitting adjustment and releasable fixing of a pose of the ultrasound transducer unit 32. The pose determines in part the field of view 34 of the transducer unit 32 relative to the patient anatomy.

The ultrasound transducer unit may be operatively connected to an ultrasound processing module or unit 42, also forming part of the ultrasound imaging apparatus. This may control the driving of the ultrasound transducers of the transducer unit 32. It may control acquisition and receive settings of the probe for example. It may define or configure the ultrasound imaging field of view 34. The ultrasound processing unit 42 may additionally receive and process ultrasound data 38 generated by the ultrasound probe. This may for example be received at the ultrasound processing unit 42 as echo data (RF data), or as partially beamformed data in some examples. In either case, the ultrasound processing unit performs ultrasound processing to derive ultrasound imaging data, for example B-mode ultrasound image data of the region covered by the field of view 34. This may take the form of data representative of a series of ultrasound images (image frames), each representative of a different time point over the course of an arbitrary imaging period. These may be generated sequentially, one-by-one, and in real time with the capturing of the ultrasound echo data by the transducer unit 32.

The ultrasound imaging apparatus 32, 42 may be comprised as part of a system provided in an aspect of the invention, or may be an external or auxiliary apparatus, with which components of a system or device provided by the invention are adapted to be in communicative connection during use.

A processing arrangement 50 is arranged to receive the series of ultrasound images (ultrasound image data) 44 output by the ultrasound imaging apparatus. For example the processing arrangement may include an input/output or a communication module (not shown) for receiving the input data.

The processing arrangement 50 is adapted to process each of the series of ultrasound images, for example each in turn, in real time, in order to determine a displacement, within a frame of reference which is fixed relative to the ultrasound imaging field of view 34, of the pre-defined reference point 24. An image processing module 52 may be included for this function.

Although a reference point is referred to, this can mean a single point or a line, e.g. an edge of an anatomical structure such as an organ. It may also or alternatively mean a volume or area. The reference point, line, volume or area whose position is to be detected may be defined by a user, for example in a configuration step preceding the acquisition or retrieval phases. This may be based on using a user interface to identify the point, line, volume or area on a sample ultrasound image of the anatomical region. This can then be used as to inform which point, line, area or volume should be tracked. Alternatively, the point, line area or volume to be tracked may be pre-set in advance. For brevity, a 'reference point' shall be referred to elsewhere in this disclosure. This should be understood as encompassing any of a point, line, area or volume as explained above.

By 'displacement' is meant for example a position within a frame of reference which is fixed relative to the ultrasound imaging field of view 34. For example a fixed co-ordinate system may be defined (e.g. in advance) which is fixed relative to this frame of reference, and the determined displacement is a position within this co-ordinate system. This may be a one dimensional, two dimensional or three dimensional co-ordinate position, depending in part on the dimensionality of the ultrasound imaging. More than one probe 32 may be used to enable multi-dimensional reference point tracking and/or volumetric ultrasound imaging can be performed. Since the ultrasound transducer unit 32 is fixed relative the surface on which the patient is resting (e.g. fixed relative to the operating room), this frame of reference is also fixed relative to this surface. By way of example, this step may comprise determining a position co-ordinate identifier (e.g. vector), P, of the reference point 24 for each image frame within a pre-defined co-ordinate system which is fixed relative to the ultrasound imaging field of view.

Determining the reference point position within each image frame may be achieved using one or more image processing algorithms which may employ for example shape-recognition or edge detection techniques to identify the relevant reference point or line. It may be based on segmentation applied to each image frame to assist with identifying the relevant anatomical point or line.

Once the relevant point has been identified in the ultrasound image frame, a displacement indicator, e.g. a position co-ordinate set or vector, can be generated. This can be based on mapping the ultrasound imaging field of view 34 to the pre-defined reference point co-ordinate system (discussed above). The co-ordinate system may be defined relative to the field of view, so that the mapping is inherently known, based on the definition of the co-ordinate system. Alternatively, a map may be determined or defined, based on a position or pose of the probe relative to the co-ordinate system. The skilled person will recognize standard mathematical techniques for achieving this.

One particularly advantageous method for performing the detection and position tracking of the reference point is based on an initial user input which indicates, within one or more of the ultrasound image frames, an area of the ultrasound field of view within which the reference point or line (e.g. an edge of an organ) is located. This simplifies the image processing algorithms necessary to identify and track the reference point (or line, area or volume) within the ultrasound image stream. This method will be described in detail later in this disclosure.

Once the reference point displacement 54 has been determined for a given ultrasound image frame, this is used to query 58 a reference image datastore 60 which stores a dataset of reference images 62 representative of the anatomical object 22 in different movement positions, and where each image is associated or linked with a corresponding recorded displacement of the reference point 24 within a frame of reference fixed with respect to the reference imaging field of view.

The process of querying 58 comprises then selecting one of the reference images which is associated with the same, or close to the same, reference point displacement as in the ultrasound image. For this, it is important that there is correspondence between the metrics (e.g. the co-ordinate systems) in which the newly measured reference point displacement 54, and the recorded reference point displacements (in the datastore 60) are represented. For example, the co-ordinate systems in which the displacements are represented should match.

For this purpose, optionally, there may be a step of a metric or co-ordinate system registration 56 or conversion. By way of example, the reference image datastore 60 may store a co-ordinate system identifier along with the dataset of reference images, allowing the co-ordinate system in which the reference point 24 positions in the dataset are recorded to be detected. The co-ordinate registration can be done based on this. In some examples, pose information for the ultrasound probe may be obtained and used for converting the co-ordinate systems, e.g. based on reference probe pose information stored in the datastore. Alternatively or additionally, co-ordinate system identifier information from the image processing unit 52 may be used.

Alternatively, the co-ordinate systems may inherently match, for example if the reference dataset 60 was acquired in an acquisition phase performed only recently in advance of the retrieval phase, with the ultrasound probe configured in the same pose relative to the anatomy as in the present retrieval phase, and with the image processing unit 52 using the same co-ordinate system definition to determine the reference point displacement.

Based on the determined displacement 54 of the reference point 24 in the received ultrasound image frame 24, at least one of the reference images 62 in the datastore is selected. An output is generated representative of the selected image, or based on the selected image.

Selecting the reference image 62 may comprise identifying a reference image with an exactly matching associated reference point displacement 24. Alternatively, where an exact match with the measured reference point displacement cannot be found, one of the reference images having an associated reference point displacement which most closely matches may be selected. Alternatively, and as will be discussed in more detail later, in some cases, a new reference image may be generated based on interpolating between two reference images which correspond to reference point displacements either side of the measured reference point displacement 54.

In each case, an output 64 is generated representative of the selected or generated reference image 62. This may be coupled or transmitted to a display device 72 for display to a user. The reference image may be displayed concurrently with display of received ultrasound image 44 to which the reference image corresponds. This may be communicated to the display unit 72 by the processing arrangement 50. A display output module may be included which receives the ultrasound image 44 and reference image 62 and generates a combined display output for coupling to the display. By way of non-limiting example, this may comprise just the reference image, or the reference image and ultrasound image side-by-side, or the ultrasound image and the reference image overlaid or superimposed (fused). Any other display format can also be used.

Viewing the images of the two modalities together may assist a clinician in noticing any differences between the live ultrasound imagery and the secondary images, which could occur during an interventional procedure, e.g. the organ of interest begins to swell because of the procedure. Optionally, when such a change is detected, the calibration or set-up phase (to be described later) may be repeated to re-acquire the reference imaging dataset.

In some examples, a co-ordinate system registration may be performed between the ultrasound imaging field of view or frame of reference and the secondary imaging modality in advance of generating the display 72 output. This may be useful for visualization purposes, so that the ultrasound images and reference images correspond to the same area of the anatomy. For example, this means that both image sets could be viewed together, as discussed above, and be shown at the same size, orientation, spatial location and, optionally superimposed (fused). Optionally, a step of image fusion may be done subsequent to co-ordinate system registration to check the accuracy of the registration. The registration may only need to be done once per imaging period or session, rather than for every received ultrasound image.

In some examples, the support frame 36 may be adapted to generate a data output 76 comprising a pose indicator indicative of a current pose position of the frame. This can be based on use of one or more electromagnetic sensors incorporated in the frame unit, adapted to sense a (3D) pose of probe held in the frame. The frame may comprise a cradle or gripping part which releasably holds the probe, and wherein this is pivotally movable relative to a support stand portion of the frame which attaches to a surface fixed relative to the surface on which the subject is resting. A pivotal position of the cradle or gripping part relative to the support stand part may be sensed using electromagnetic or any other suitable sensor (e.g. optical).

In some examples, the frame may be electronically actuable to move a held ultrasound probe to a defined pose, and wherein the pose is precisely or uniquely identifiable by an electronic identifier signal or code. This can be used to ensure that the probe is configured in the same pose position as was used to measure the reference point 24 displacement when acquiring the reference images (as will be explained further later).

The output signal indicative of the pose may additionally or alternatively be used in performing co-ordinate system transformation or registration between the ultrasound probe frame of reference and a frame of reference for the secondary imaging modality (discussed above), or between the probe co-ordinate system and that used by a probe in measuring the displacement of the reference point during a set-up phase.

By way of example WO 2019/110115 describes an example frame unit whose position is electronically trackable. The frame is described with reference to application for a hair cutting device. However, the same principles may be applied to provide a pose-trackable holding unit for an ultrasound probe. Tracking of a position and orientation in space (i.e. pose) of a unit, for example using electromagnetic sensing, is a well-known technology and the skilled person will be aware of means for implementing this. Off-the-shelf solutions for electromagnetic pose tracking are known.

More than one ultrasound transducer unit 32 can be used to track the reference point in some examples. This can enable determining reference point displacement in multiple dimensions.

It is noted that use of an ultrasound probe is not essential. Other examples of an ultrasound transducer unit include use of an ultrasound monitoring patch which can be adhered to a skin surface in a reliable position, and remains fixed in place throughout the procedure.

FIG. 3 schematically illustrates the reference imaging dataset stored by the reference datastore 60. The reference dataset comprises a plurality of reference images 62a-62e. Only five reference images are shown in FIG. 3, but more than five may typically be included. Each reference image is associated in the dataset with a time point during the imaging period, and associated with a displacement indicator, P, of the reference point 24 at the time the reference image was captured. This is shown in form of a three-dimensional vector, but it may take any form, including (by way of non-limiting example) a 1D or 2D vector, or a 1D or 2D co-ordinate set.

As will be explained later, preferably the imaging dataset corresponds to a series of images covering a movement cycle of a cyclically moving anatomical area or body, and thus the time stamps of the images may correspond to time points within said movement cycle.

As discussed above, the reference images 62 of the dataset 60 are images previously acquired for the same anatomical object 22 during a set-up or calibration phase, and wherein the associated displacement 54 of the reference point 24 for each reference image is a displacement recorded in a simultaneously acquired ultrasound image 44 relative to a frame of reference fixed with respect to the ultrasound imaging field of view.

This set-up or calibration phase will now be described, with reference to FIG. 4 which shows, in block diagram form, steps of an example method for performing the set-up or calibration phase in accordance with one or more embodiments.

In particular, an aspect of the invention provides a method 100 of generating a dataset 60 of reference images 62 of a moving anatomical object 22 for use in providing a source of secondary imaging.

According to one or more embodiments, the method 100 comprises acquiring 102, using a first imaging modality 82, a series of first images 62 of an anatomical region containing the anatomical object over an imaging period.

The method 100 further comprises, simultaneously with the acquiring of the series of first images, acquiring 104 a series of ultrasound images 44 of a region containing the same anatomical object over said imaging period, wherein the first imaging modality 82 is different to that of the ultrasound images.

The method 100 further comprises, for each of the ultrasound images, determining 106 a displacement, within a frame of reference fixed with respect to the ultrasound imaging field of view, of a pre-defined reference point 24 fixed relative to the anatomical object.

The method 100 further comprises, for each of the first images, storing 108 in a dataset a representation of the first image and an associated record of the determined displacement of the reference point within one of the ultrasound images acquired simultaneously with the first image, to thereby generate a reference imaging dataset 60 for providing a source of secondary imaging.

Figure 5:
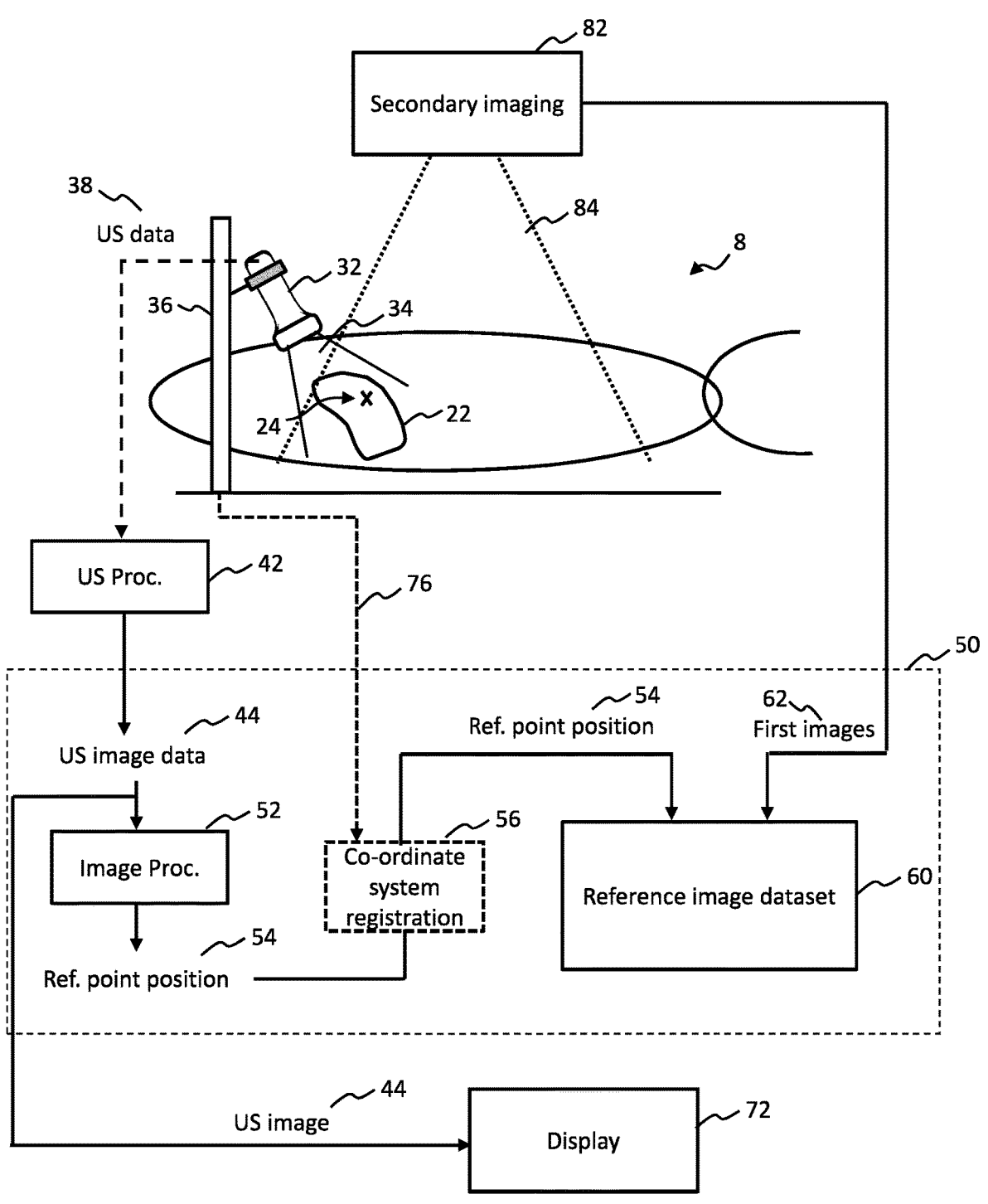
FIG. 5 illustrates an example workflow according to one or more embodiments of the second aspect of the invention.

FIG. 5 outlines an example workflow for performing the calibration or acquisition phase. Most of the steps performed in this phase are the same as those in the recall or retrieval phase discussed above, except that secondary imaging is performed simultaneously with acquisition of the ultrasound images, using a secondary imaging modality 82, and the reference images are not retrieved from a reference image dataset 60, but rather are stored in the dataset along with a determined displacement of the anatomical reference point 24. Similar steps or components will thus not be described in detail again here, and the reader is referred to descriptions provided previously in relation to the retrieval phase.

The ultrasound transducer unit 32 may be set up in the same pose relative to the patient anatomy as in the subsequent retrieval phase. As in the retrieval phase, ultrasound images are acquired continuously or recurrently of the anatomical area containing the object of interest 22, and including the defined reference point 24. The ultrasound data from the probe is processed 42 to derive ultrasound images 44. The displacement of the reference point 24 in each ultrasound image frame is determined, for example using an image processing unit 52, as discussed previously. Simultaneously with ultrasound imaging, a secondary imaging modality 82 such as MRI, CT, X-ray fluoroscopy or any other imaging modality, acquires a set of first images 62 (which correspond to the reference images retrieved in the retrieval phase). For each secondary image frame (2D or 3D), this is stored in a datastore 60 in association with a measured displacement of the anatomical reference point 24 within the ultrasound imaging frame of reference for an ultrasound image frame captured simultaneously with the relevant secondary image frame. In this way, a dataset of reference images is formed, each associated with a measured displacement of the reference point 24 within a frame of reference fixed relative to the ultrasound imaging field of view and the secondary imaging field of view. This hence effectively forms an indexed dataset of reference images, where the indexing is done via the 1D, 2D or 3D measured displacement of the reference point.

As discussed above, the displacement of the reference point 24 may be expressed or recorded in terms of a set of one or more co-ordinates, or a vector. The co-ordinate system or metric used to represent the displacement of the reference point should be consistent with that used to measure the displacement in the subsequent retrieval phase. Thus, a record may be made in the dataset 60 to indicate what metric or co-ordinate system is being used. Optionally, a process of registration or conversion 56 of the co-ordinate system or metric for the displacement measurement may optionally be performed in advance of recording it in the dataset, for instance to convert the displacement to a common co-ordinate system.

The acquired ultrasound images 44 may additionally be streamed in real time to a display unit 72. In preferred examples, the secondary images may also be output in real time to the display unit. This allows for example a user to check in real time that the acquired ultrasound and secondary images correspond in terms of the anatomical area being imaged.

Optionally, the retrieval phase 10 discussed above may be performed immediately following the acquisition or set-up phase 100. For example, the patient is moved out of the high resolution image modality (e.g. moved out of the MRI or CT scanner), while keeping the ultrasound probe(s) in the same position (e.g. using the configurable frame 36). Optionally, the reference imaging dataset can be reacquired (by repeating the acquisition phase) at multiple points during a medical procedure, to keep the imaging up-to-date.

According to an advantageous set of embodiments, the anatomical object 22 is a cyclically moving anatomical object and the imaging period (over which the reference images are captured, and subsequently retrieved) corresponds to one or more movement cycles of the anatomical object. For example, the anatomical object may be the whole or part of the heart, or lungs. Furthermore, many organs or anatomical areas of the body exhibit secondary cyclical movement caused by the breathing cycle. For example the liver moves cyclically due to application of pressure from the diaphragm between the lungs and the liver.

The stored dataset 60 may comprise a set of reference images 62 corresponding to a series of time points which span a complete movement cycle of the anatomical object. In this way, high resolution reference images are available for times which span the whole cycle of movement periods of the object.

Figure 6:
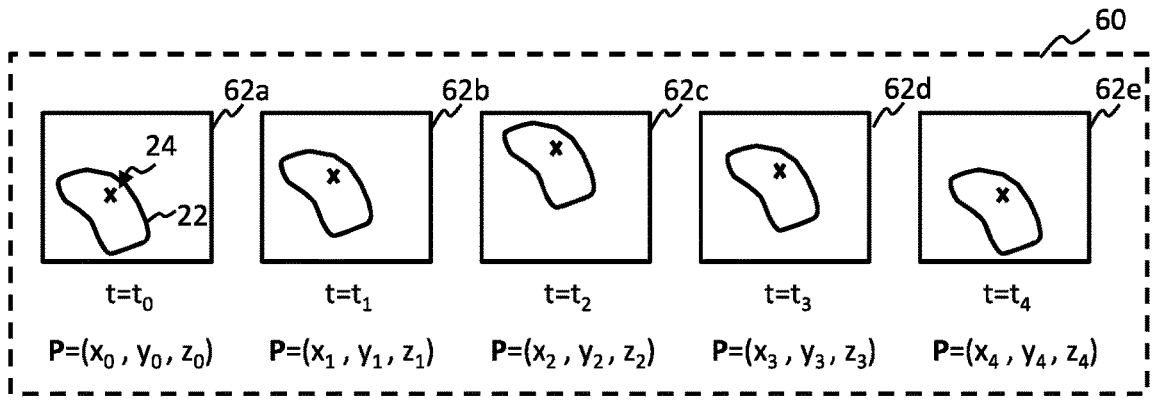
FIG. 6 schematically illustrates an example reference imaging dataset for an imaging period covering a complete movement cycle of a cyclically moving object.

FIG. 6 schematically illustrates an example reference imaging dataset 60 comprising a set of reference images 62a-62e corresponding to different time points throughout the course of a movement cycle of the object of interest 22 and the associated reference point 24. Although only five images are shown in the illustrated example, typically a greater number of reference images would be stored. As schematically depicted, each reference image represents the object of interest 22 and the reference point 24 at a different respective spatial positioning within the imaging frame of reference.

Since the secondary imaging modality 82 typically has a lower temporal resolution than the ultrasound imaging, over the course of a single movement cycle of the object of interest 22, typically a greater number of ultrasound image frames will be acquired compared to the number of image frames of the secondary (high resolution) imaging modality 82. Thus, over a single movement cycle, there will not be recorded a corresponding higher resolution reference image for every detected position of the reference point 24 within the ultrasound images over the course of the cycle. Thus, to build up a more complete imaging dataset for the movement cycle, in the acquisition or setup phase 100, the imaging may be performed over the course of a plurality of movement cycles of the object of interest, and wherein the secondary images 62 acquired over the plurality of cycles are compiled into an aggregate dataset. Since there will typically not be complete temporal alignment between the imaging times of the secondary imaging modality in each of the cycles, the aggregate dataset will comprise a set of secondary images covering a greater number of time points throughout the movement cycle compared to the images acquired during any one of the cycles alone.

Figure 7:
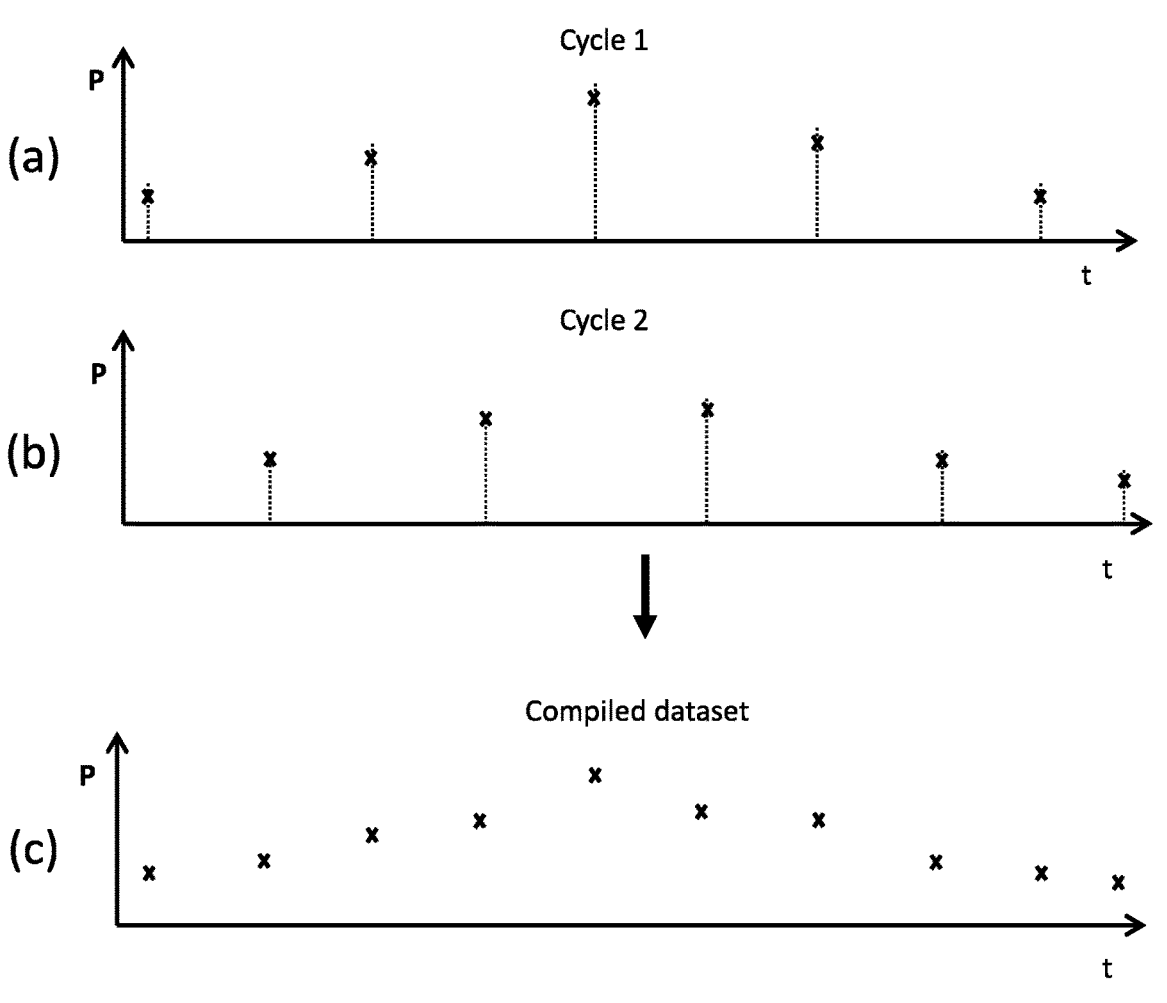
FIG. 7 schematically illustrates formation of a compiled dataset comprising reference images captured at different phase points over each of two different movement cycles of a cyclically moving object.

This is illustrated schematically in FIG. 7. FIG. 7(a) schematically represents the detected displacements, P, of the reference point 24 in secondary image frames acquired at a series of time points over the course of a first movement cycle. FIG. 7(b) schematically represents the detected displacements, P, of the reference point 24 in secondary image frames acquired at a series of time points over the course of a second movement cycle. FIG. 7(c) shows the compiled (aggregate) secondary imaging dataset with the secondary images from both the first and second cycles included together. As shown, this includes images corresponding to a greater number of time points (or phase points) over the movement cycle than any one of the cycles alone. In practice, imaging for more than two cycles may be performed. The compiled or aggregate imaging dataset (FIG. 7(c)) may inherently be formed through the process of appending each generated reference image to the reference image dataset 60 over the course of an imaging period spanning several movement cycles. Since the images are indexed in the dataset according to the position of the reference point, an aggregated dataset over multiple movement cycles of the reference point is automatically built up.

If the acquisition or set-up phase 100 is performed over the course of a sufficiently large number of movement cycles, e.g. 5-10, this should be sufficient to build up a reference imaging dataset 60 comprising a corresponding secondary (higher resolution) image for every one of the ultrasound image frames (i.e. for every detected position of the reference point 24). However, in some instances, this may not be possible (e.g. if the acquisition phase is only run for a limited period of time).

In accordance with one or more embodiments, there may be included functionality for generating an interpolated secondary image frame (during the retrieval phase 10) in the event that a displacement of the reference point 24 is measured which does not exactly match the displacement recorded for any of the reference images 62 in the dataset.

Figures 8, 9:
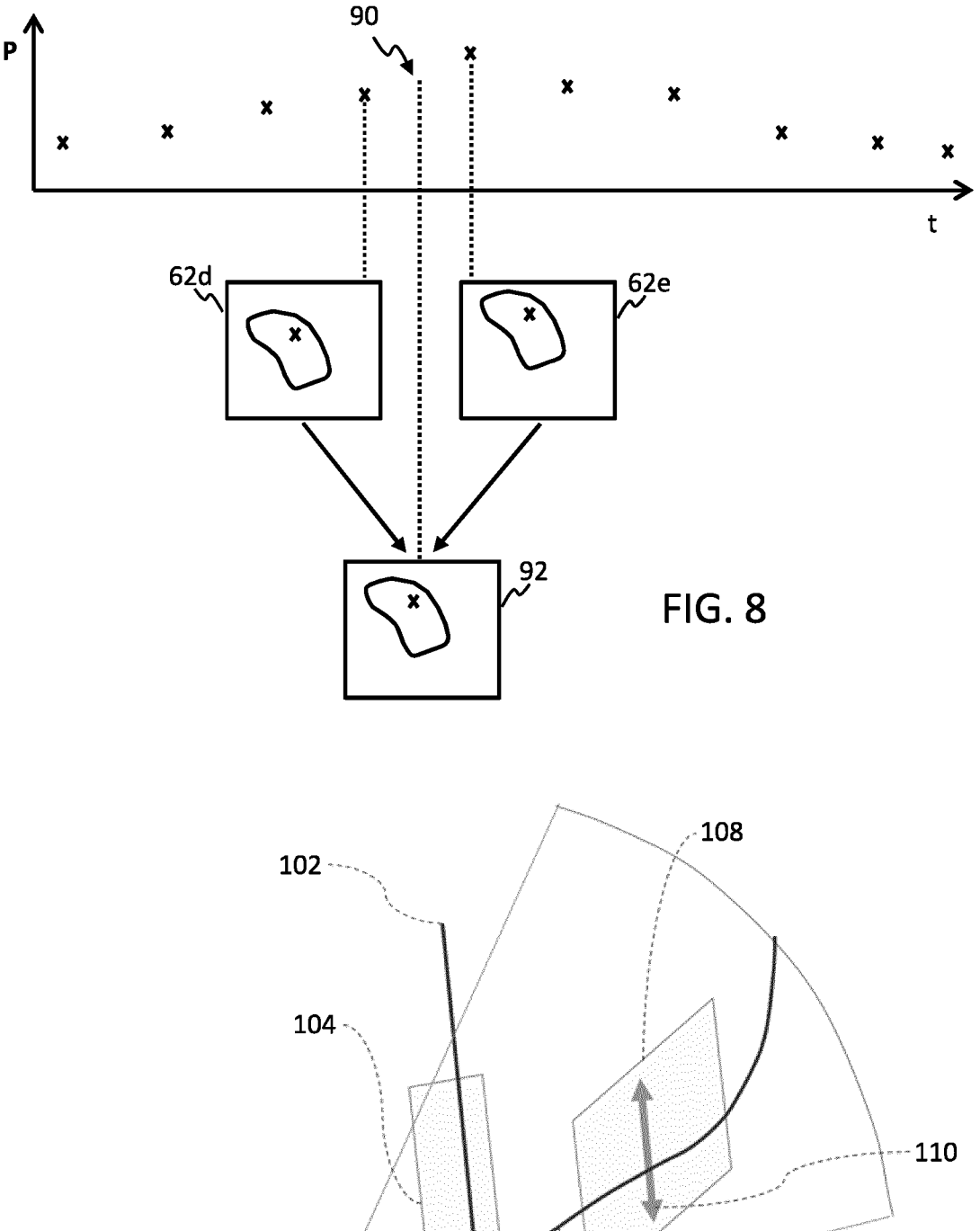
FIG. 8 schematically illustrates interpolation of a secondary image for a movement position of an imaged object which is intermediate movement positions for two recorded reference images.
FIG. 9 schematically illustrates a step within one example method for detecting and tracking a displacement of a reference line within received ultrasound images.

This is illustrated schematically in FIG. 8. This schematically illustrates measured reference point displacements, P, for a dataset of reference images acquired during an acquisition phase 100. During the retrieval phase, a reference point 24 displacement 90 is detected which falls intermediate is intermediate (in-between) the recorded reference point displacements of an example first 62d and second 62e of the reference images. Responsive to determining this, an interpolated reference image 92 is generated based on interpolation between the first and second of the reference images.

This could be generated for example simply by taking an average (median or mean) of the pixel intensity values of the first 62d and second 62e reference images between which the detected reference point displacement 90 falls. This would result in an image frame which lies between the two frames. However, this approach may result in loss of resolution.

Another, more sophisticated, way to determine an interpolated image frame is to use motion estimation techniques to estimate motion of the moving anatomical object between the first 62d and second 62e reference images, and, based on this, determine an estimated position of the anatomical object at the intermediate reference point position 90. A similar approach is used in the technical field of televisions, and is referred to as scan-rate conversion. One example methodology is outlined in the paper: G. De Haan and P. W. A. C. Biezen, "An efficient true-motion estimator using candidate vectors from a parametric motion model," in *IEEE Transactions on Circuits and Systems for Video Technology*, vol. 8, no. 1, pp. 85-91, February 1998. This approach is based on motion detection and prediction.

As an alternative to interpolation, responsive to detecting that the determined displacement 54 of the reference point in a received image does not match the recorded reference point displacement of any of the reference images 62 in the dataset 60 and is intermediate the recorded reference point displacements of a first and second of the reference images, the method may comprise selecting one of the first or second reference images and generating the output 64 indicative of the selected one of these images. Hence here, one of the reference images closest to the detected reference point position is selected in place of a reference image of the object of interest with the reference point at the exact detected reference point position.

The method may comprise determining which of (the reference points of) the first and second reference images the determined displacement 54 of the reference point in the received image is closest to, and select the identified closest image to use for generating the output 64.

As discussed above, there are different possible methods for detecting the reference point 24 displacement within the received series of ultrasound images 44. One advantageous approach will now be outlined in more detail. This approach is outlined by way of one example only and other method can alternatively be used, as discussed above.

The approach discussed below aims to provide a simplified algorithm for tracking of a displacement of a reference point 44 or line on an object of interest. It provides advantages of reduced computational complexity compared to other algorithms, such as those based on so-called 'optical flow motion tracking'. The approach is based on receiving an input from a user interface indicative of a region or area within which a particular reference point or line to be tracked is located. Thus, the user provides assistance to the detection algorithm. This requires very little human cognition time, but saves a large amount of computing resource. The approach is preferably based on tracking one or more edges of the object of interest.

The approach comprises a user providing a user-input based on their observations of the live ultrasound image stream 44 received from the ultrasound apparatus 32, 42 and displayed on the display 72. The user-input may be provided via a graphical user interface for example.

In particular, the user performs the following actions based on their observations. First, the user delineates one or more areas of interest in the live ultrasound stream. A user interface is provided having a user input device (e.g. a pointer, mouse, touch screen, or electronic pen) and which is adapted to receive the user input indicative of the delineation. The graphical user interface for drawing the edges preferably may support dragging, resizing and deformation of boundaries of the one or more areas. The interface may include enforced snapping of the delineated area into a parallelogram shape during (or after) each user interaction. The selection of example areas of interest is schematically illustrated in FIG. 9.

The selected area(s) 108 are chosen so as to enclose a part of an edge 106 of the object of interest, this edge being the reference point 24 or line whose displacement is to be detected and tracked throughout all of the received ultrasound image frames. The edge 106 is schematically illustrated in FIG. 9. By way of example, FIG. 9 shows an edge which represents a boundary of a subject's liver. The liver may undergo cyclical movement due to pressure applied by the diaphragm as a result of breathing.

For a moving edge, two boundaries of the delineated area 108 should be as parallel as possible with the direction 110 of the motion. This ensures that a moving structure of interest remains in the area of interest at all times.

The other two boundaries of the area 108 should be as parallel possible to the direction of the edge 106 to be tracked. This ensures maximum enhancement of the edge of interest, as the algorithm uses this to set the direction for pixel averaging (explained later).

As an additional, optional feature, other edges, not related to the object of interest, may also be tracked. For example, FIG. 9 shows a user-selected area 104 containing an edge 102 formed by the contact plane between the subject's 8 body and the support surface on which the subject 8 and the transducer unit 32 are resting. Monitoring of changes to a displacement of this edge can be used to provide an indication that the patient is moving for example, which may be used to inform registration between the ultrasound and secondary imaging fields of view or frames of reference, or to adjust the registration 56 of the ultrasound co-ordinate system.

In accordance with some examples, the boundaries of the area(s) of interest may be automatically modified or updated during the course of the reference point tracking (over the plurality of ultrasound image frames 44). For example, an optimization algorithm may be employed which is adapted to assess the user-delineated boundaries of the area(s) of interest and modify them in terms of length or directionality so as to ensure that the reference line or edge is inside the area throughout the course of its movement.

Figure 10:
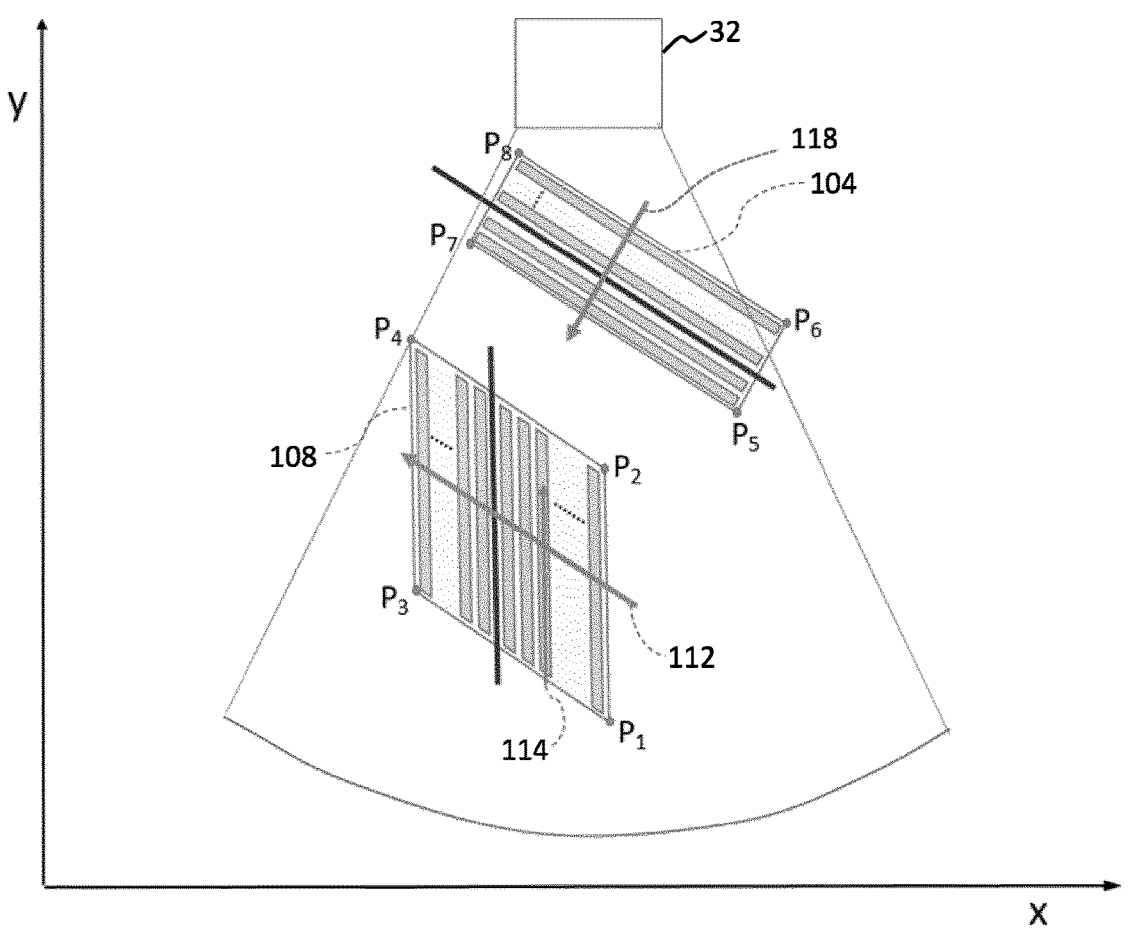
FIG. 10 schematically illustrates a further step within the example method of FIG. 9 for detecting and tracking a displacement of a reference line within received ultrasound images.
Figure 11:
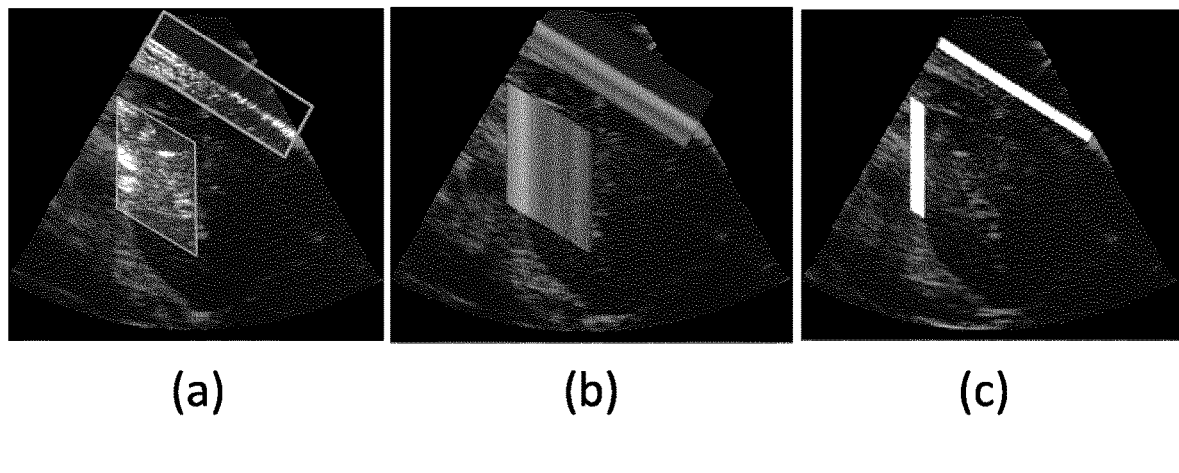
FIG. 11 illustrates the effect of different stages within one step of the example method for detecting and tracking a displacement of a reference line within received ultrasound images.

Once the user-input delineation of the area 108 containing the reference point or edge 106 has been received, the method comprises computing a location of the edges. This can be done by an algorithm which comprises the steps as set out below. Some of the steps of the algorithm are schematically illustrated in FIG. 10. FIG. 11 shows the ultrasound image frame at three different stages of the algorithm. FIG. 11(*a*) shows the delineation of the one or more areas of interest 108, 104 as discussed above.

The steps of the algorithm are as follows.

First, within the image frame in which the area of interest 108 has been delineated, the area of interest 108 is notionally divided into elongate strips, the strips constructed or defined having an elongate extension along a direction of the border of the area 108 which runs parallel the edge 106 being tracked. The strips may be contiguous so that they cover the whole of the area of interest. The strips may be of equal width, or at least a majority of the strips may be of equal width.

The division of each area into strips is schematically illustrated in FIG. 10, which shows the process performed for the area 108 containing the edge 106 of the organ, and the optional area 104 containing the subject-surface boundary edge 102.

The algorithm further comprises summating the pixel intensity values of pixels inside each strip and computing an average pixel intensity value for the whole strip. The average means an arithmetic mean for example. The summating for each strip is schematically illustrated by arrow 114 in FIG. 10.

The algorithm further comprises, for each strip, replacing the pixel intensity value of each pixel with the average intensity value determined for the respective strip. It is noted that by creating strips along the direction of the tracked edge 106 and summing the pixel values in each strip, typically blurry organ areas are enhanced, while typically noisy, speckled 'empty' space will receive a more uniform grey level with low intensity. This is illustrated in FIG. 11*b* which shows the areas of interest 108, 104 after the pixel averaging for the strips has been performed.

To detect the edges, the algorithm comprises the following further steps.

Local averaging and pixilation is applied to increase the smoothness of the image and reduce pixel resolution.

A suitable threshold is applied to create a sharp edge between the object of interest and the surrounding space. This is illustrated in FIG. 11(*c*).

A middle of the edge is computed based on two steps. First, a line is defined which runs through all the strips in the, or each, delineated area of interest 108, 104, from a midpoint of the bottom-most or left-most strip to a mid-point of the most top-most or right-most strip. FIG. 10 illustrates the defined line 112 for the delineated area 108 and the defined line 118 for the delineated area 104. The middle of the edge is then found by comparing pixel intensity values of neighboring strips along the line. The neighboring pair of strips with the largest difference in their respective pixel intensity values, or a difference which exceeds a pre-defined threshold, can be assumed to coincide spatially with the boundary line.

This edge detection process is done for each of the received ultrasound images of the series of ultrasound images. This allows for the displacement of the edge within each image frame to be precisely determined.

Certain of the above steps will now be described in more detail.

To understand the explanations, a mathematical description of the strips relative to the one or more areas of interest 104, 108 will first be described with reference to FIG. 10.

Let $S_{(x_d, y_d)}$ represent a (thin) strip with right-hand side coordinate $(x_d, y_d)$ in the optional area of interest 104 shown in FIG. 10. For this strip, the following holds $$x_{P_5} \leq x_d \leq x_{P_6} \qquad \text{(eq. 1)}$$

$$y_d = \frac{y_{P_6} - y_{P_5}}{x_{P_6} - x_{P_5}} \cdot (x_d - x_{P_5}) + y_{P_5} \qquad \text{(eq. 2)}$$

By for example incrementing $x_d$ from $x_{P_5}$, to $x_{P_6}$, iteration over all the strips in this example area 104 is achieved. The example area 104 shows two strips below the edge and an undetermined number of strips above the edge—see FIG. 10. The total number of strips however may typically be many more than are shown in FIG. 10. A single strip may be only a few pixels wide, e.g. 1-5 pixels.

If $(x_s, y_s)$ denotes the coordinate of a pixel inside strip $S_{(x_d, y_d)}$, then the full set of pixel coordinates for this strip may be described by:

$$x_d \geq x_s \geq x_d + x_{P_7} - x_{P_5} \qquad \text{(eq. 3)}$$

$$y_s = \frac{y_{P_7} - y_{P_5}}{x_{P_7} - x_{P_5}} \cdot (x_s - x_d) + y_d \qquad \text{(eq. 4)}$$

This holds under the condition that the opposite edges of the delineated area 108, 104 are parallel to one another (and equally sized), i.e. the area is a parallelogram.

In case the area 108, 106 has (near) horizontal and/or vertical edges, iteration and summing should be done over suitable axes to achieve sufficient resolution in the number of strips and the number of pixels per strip. For example, for the area 108 containing the reference edge 106, the right-hand and left-hand edges of the area 108 are (approximately) vertical and are parallel to the strip direction in this area (see FIG. 10). This would result in inaccuracies in the enumeration of pixels in each strip. In particular, it is noted that eq. 3 and eq. 4 above require $P_5$ and $P_7$ to be replaced by $P_1$ and $P_2$ respectively (and $P_6$ by $P_3$) for the area 108. Since $x_{P_1}$ is very close to $x_{P_2}$ this would result a very small range for enumeration. Following eq. 3, this would be $$x_d \geq x_s \geq x_d + x_{P_2} - x_{P_1} - x_d$$

Following eq. 4, it also may result in an inaccurate result for $y_s$ due to the division by $x_{P_2} - x_{P_1}$.

It is noted however that iteration over the different strips in area 108 can be done over either the x-axes or the y-axes, since the x and y coordinates of $P_1$ and $P_3$ are sufficiently different (see FIG. 10).

If both iteration over strips and pixel enumeration within strips is done over the y-axes in the area 108, this leads to the following modifications to eq. 1, eq. 2, eq. 3 and eq. 4:

$$x_{P_1} \leq y_d \leq y_{P_3} \qquad \text{(eq. 1b)}$$

$$x_d = \frac{x_{P_3} - x_{P_1}}{y_{P_3} - y_{P_1}} \cdot (y_d - y_{P_1}) + x_{P_1} \qquad \text{(eq. 2b)}$$

$$y_d \leq y_s \leq y_d + y_{P_2} - y_{P_1} \qquad \text{(eq. 3b)}$$

$$x_s = \frac{x_{P_2} - x_{P_1}}{y_{P_2} - y_{P_2}} \cdot (y_s - y_d) + x_d \qquad \text{(eq. 4b)}$$

Depending on the direction of the edges of the area 108 and the strip direction inside the area, the most accurate method of strip iteration must be selected, i.e. either according to eq. 1 or 2, or according to eq. 1b or 2b. The same may be applied to pixel enumeration within a strip, where this may be performed either according to eq. 3 or 4, or eq. 3b or 4b. Herein, pixel enumeration refers to the process of iterating through all of the pixels inside a single strip and performing the steps discussed above of summating the pixel values, computing the average pixel value for each strip, updating the pixel values with the computed average value, and performing the thresholding step.

Details relating to the feature of summating pixel values within a strip will now be discussed.

By summing the intensity values of all pixels within a strip and replacing each pixel in the strip by the average pixel value for the strip, strong edge enhancement is achieved. This can be seen in FIG. 11(*b*) which shows an example ultrasound image frame after this procedure has been performed.

The average pixel value means for example the arithmetic mean, computed as the sum of the pixel intensity values of all pixels in a given strip, divided by the number of pixels in the strip.

FIG. 11(*a*) shows the areas of interest 104, 108 as graphics overlays in an ultrasound image frame. The result of pixel intensity summation within strips is shown in FIG. 11(*b*).

The process of pixilation and threshold application will now be discussed.

The modified strips are converted into black and white images by applying a threshold T, which changes each pixel value to either zero or the maximum allowed pixel value $I^{max}$, dependent upon whether the original pixel value is below or above the threshold T respectively.

If $I''_{(x_s, y_s)}$ denotes the value of a pixel at coordinate $(x_s, y_s)$ in strip $S_{(x_d, y_d)}$ after threshold, while $I'_{(x_s, y_s)}$ denotes the averaged pixel value at the same coordinate (see above), then the following holds:

$$I''_{(x_s,y_s)} = 0, \text{ for } I'_{(x_s,y_s)} < T$$

$$I''_{(x_s,y_s)} = I^{max}, \text{ for } I'_{(x_s,y_s)} \leq T$$

Ultrasound images have typically 8 bit pixel values, hence $I^{max} = 255$ in this case.

When the pixilation and thresholding is done for both the example areas 108, 104 of FIG. 11$b$, the result as depicted in FIG. 11($c$) is achieved.

The process of detection of the middle of the tracked edge 106, 102 will now be discussed.

After applying the threshold, as described above, the strips in the relevant area of interest 108, 104 are intersected by a line running through the middle of the strips, such as depicted by the arrow 112 or 118 in FIG. 10.

For example, if $(x_l, y_l)$ denotes a point on such a line 118 for the optional area of interest 104, the following holds:

$$\frac{x_{P_6} + x_{P_8}}{2} = \frac{x_{P_5} + x_{P_7}}{2} + x_{P_6} - x_{P_5} \geq x_l \geq \frac{x_{P_5} + x_{P_7}}{2} \qquad \text{eq. 5}$$

$$y_l = \frac{y_{P_6} - y_{P_5}}{x_{P_6} - x_{P_5}}\left(x_l - \frac{x_{P_5} + x_{P_7}}{2}\right) + \frac{y_{P_5} + y_{P_7}}{2}. \qquad \text{eq. 6}$$

By comparing pixel values along this line 118, the intersection with the tracked edge 102 of interest is found at coordinate $(x_i, y_i)$, if the intensity values of adjacent pixels differ significantly, e.g. by a pre-defined threshold amount. The sharp contrast in pixel intensity values at the boundary of the edge is guaranteed by the thresholding procedure previously applied. For example, at the location of the edge, the following holds:

$$I''_{(x_i, y_i)} >> I''(x_{i+1}, y_{i+1}), \text{ or } I''_{(x_i, y_i)} << I''_{(x_{i+1}, y_{i+1})}$$

where $x_{i+1} = x_i + 1$ and where $(x_i, y_i)$ and $(x_{i+1}, y_{i+1})$ satisfy eq. 5 and eq. 6 above.

The computed edge $E_i$ is may then be assumed to run across the area of interest 104, 108 in the elongate direction of the strip (see FIG. 10):

$$E_i = \left(x_i - \frac{x_{P_7} - x_{P_5}}{2}, y_i - \frac{y_{P_7} - y_{P_5}}{2}\right) \text{ to } \left(x_i + \frac{x_{P_7} - x_{P_5}}{2}, y_i + \frac{y_{P_7} - y_{P_5}}{2}\right)$$

The above-described process (algorithm) is performed for each of the received ultrasound images 44 in order to determine the reference line in each image. The user is only required to provide the user input delineating the areas of interest (e.g. 104 and 108 in FIG. 10) once. By default, the algorithm then applies the same delineations for each of the set of received ultrasound images. As discussed above, in some examples, the area of interest delineations may be automatically modified or adjusted based on an optimization function.

Although in the above-described example, the user selects an area of interest using the user interface device, in one variant of the approach, the user may instead delineate, using a user interface, the reference line or edge itself which is to be tracked. For example, a user interface may permit a user to draw along the line or edge 106, 102 to be tracked. The algorithm may be adapted to define the set of strips so as to follow the shape or curvature of the delineated edge or line. Thus, the strips in this example may be curved instead of straight.

The above-described algorithm represents just one example means for determining the reference point displacement in each of the received ultrasound images 44, where the reference point to be tracked is a reference line corresponding to an edge 112 of the object of interest.

Other methods for reference point, line, area or volume detection and displacement determination in each frame can be used. For example, model-based segmentation algorithms could be used to identify a desired edge or point of an anatomical object in each frame, or standard shape-matching algorithms, or edge-detection algorithms may be used.

By way of one illustrative example, one approach is described in the paper: Hideki Yoshikawa et al, "Ultrasound Sub-pixel Motion-tracking Method with Out-of-plane Motion Detection for Precise Vascular Imaging", Ultrasound in Medicine & Biology, Volume 46, Issue 3, 2020, Pages 782-795.

By way of a further illustrative example, a further approach is described in the paper: Cornel Zachiu, et al, "An improved optical flow tracking technique for real-time MR-guided beam therapies in moving organs", IEEE International Symposium on Biomedical Imaging (ISBI 2016), April 2016.

An aspect of the invention also provides the processing arrangement 50 discussed above, and configured to perform any of the methods outlined above, including one or both of the set-up (acquisition) 10 and the retrieval 100 phases. Preferably the same processing arrangement can selectively perform each of the phases, responsive to receipt of a control command signal, e.g. from a user interface, or from a further control module which co-ordinates the overall imaging system.

Although FIG. 2 and FIG. 5 show the processing arrangement 50 comprising the reference image dataset 60, this is optional. In further examples, the dataset may be external to the processing arrangement, and the processing arrangement comprises an input/output or communication module for communicatively connecting with the dataset.

Certain embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A method of providing a source of secondary imaging of a moving anatomical object of interest of a patient, the method comprising:

receiving one ultrasound image representative of an area containing the anatomical object, the image corresponding to a time point during an imaging period;

determining for the ultrasound image a displacement, within a frame of reference fixed with respect to the ultrasound imaging field of view, of a pre-defined reference point fixed with respect to the anatomical object;

accessing a dataset comprising a set of reference images representative of the anatomical object in different movement positions, the reference images corresponding to a different imaging modality to the ultrasound image, and wherein each reference image is associated in the dataset with a corresponding recorded displacement of said reference point fixed with respect to the anatomical object and within a frame of reference fixed with respect to the reference imaging field of view;

selecting, for the received ultrasound image, at least one of the reference images based on the determined displacement of the reference point in the received image;

generating after the accessing step, an interpolated reference image, responsive to detecting that the determined displacement of the reference point in the received image does not match the recorded reference point displacement of any of the reference images in the dataset and is intermediate the recorded reference point displacements of a first and second of the reference images, the interpolated reference image being generated based on interpolation between the first and second of the reference images; and generating for the received ultrasound image an output representative of one of the the selected reference image and the interpolated reference image, the output providing a source of secondary imaging.

2. A method as claimed in claim 1, further comprising displaying each selected reference image on a display device concurrently with the corresponding received ultrasound image.

3. A method as claimed in claim 1, wherein the ultrasound image is received in real time during an interventional procedure.

4. A method as claimed in claim 1, wherein the anatomical object is a cyclically moving anatomical object and the imaging period corresponds to one or more movement cycles of the anatomical object.

5. A method as claimed in claim 4, wherein the stored dataset comprises a set of said reference images corresponding to a series of time points which span a complete movement cycle of the anatomical object.

6. A method as claimed in claim 1, wherein the dataset of reference images are images previously acquired for the same anatomical object during a calibration phase, and wherein the associated displacement of the reference point for each reference image is a displacement recorded in a simultaneously acquired ultrasound image relative to a frame of reference fixed with respect to the ultrasound imaging field of view.

7. A method as claimed in claim 1, wherein the ultrasound image is received from an ultrasound imaging apparatus which comprises an ultrasound transducer unit in a fixed pose relative to the patient anatomy, and wherein the ultrasound transducer unit is held by a support frame permitting adjustment and releasable fixing of a pose of the ultrasound transducer unit.

8. A method comprising:

a calibration phase comprising performing a method comprising the steps of:

acquiring, using a first imaging modality, a series of first images of an anatomical region containing the anatomical object over an imaging period, simultaneously with the acquiring of the series of first images, acquiring a series of ultrasound images of a region containing the same anatomical object over said imaging period, wherein the first imaging modality is different to that of the ultrasound images;

for each of the ultrasound images, determining a displacement, within a frame of reference fixed with respect to the ultrasound imaging field of view, of a pre-defined fixed reference point on the anatomical object;

for each of the first images, storing in a dataset a representation of the first image and an associated record of the determined displacement of the reference point within one of the ultrasound images acquired simultaneously with the first image, to thereby generate a reference imaging dataset for providing a source of secondary imaging; and a retrieval phase, subsequent to the calibration phase, comprising performing a method comprising the steps of:

receiving one ultrasound image representative of an area containing the anatomical object, the image corresponding to a time point during an imaging period;

determining for the ultrasound image a displacement, within a frame of reference fixed with respect to the ultrasound imaging field of view, of a pre-defined reference point fixed with respect to the anatomical object;

accessing a dataset comprising a set of reference images representative of the anatomical object in different movement positions, the reference images corresponding to a different imaging modality to the ultrasound image, and wherein each reference image is associated in the dataset with a corresponding recorded displacement of said reference point fixed with respect to the anatomical object and within a frame of reference fixed with respect to the reference imaging field of view;

selecting, for the received ultrasound image, at least one of the reference images based on the determined displacement of the reference point in the received image;

generating after the accessing step, an interpolated reference image, responsive to detecting that the determined displacement of the reference point in the received image does not match the recorded reference point displacement of any of the reference images in the dataset and is intermediate the recorded reference point displacements of a first and second of the reference images, the interpolated reference image being generated based on interpolation between the first and second of the reference images; and generating for the received ultrasound image an output representative of one of the selected reference image and the interpolated reference image, the output providing a source of secondary imaging, wherein the reference imaging dataset generated in the calibration phase is used as the dataset of reference images in the retrieval phase.

9. A processing arrangement, arranged to provide a source of secondary imaging of a moving anatomical object of interest of a patient, the processing arrangement adapted to:

receive an ultrasound image representative of an area containing the anatomical object, the image corresponding to a time point during an imaging period;

determine for the ultrasound image a displacement, within a frame of reference fixed with respect to the ultrasound imaging field of view, of a pre-defined fixed reference point on the anatomical object;

access a dataset comprising a set of reference images representative of the anatomical object in different movement positions, the reference images being of a different imaging modality to the ultrasound image, and wherein each reference image is associated in the dataset with a corresponding recorded displacement of said reference point on the object within a frame of reference fixed with respect to the reference imaging field of view;

select, for the received ultrasound image, at least one of the reference images based on the determined displacement of the reference point in the received image;

generating after the accessing step, an interpolated reference image, responsive to detecting that the determined displacement of the reference point in the received image does not match the recorded reference point displacement of any of the reference images in the dataset and is intermediate the recorded reference point displacements of a first and second of the reference images, the interpolated reference image being generated based on interpolation between the first and second of the reference images; and generate for the received ultrasound image an output representative of one of the selected reference image and the interpolated reference image, the output providing a source of secondary imaging.

10. A system, comprising:

a processing arrangement as claimed in claim 9; and an ultrasound imaging apparatus comprising an ultrasound transducer unit, the imaging apparatus for acquiring the ultrasound images of the anatomical body, and arranged to communicate the acquired ultrasound images to the processing arrangement.

11. A system as claimed in claim 10, further comprising a support frame arranged to hold the ultrasound transducer unit releasably fixed in an adjustable pose relative to the patient anatomy, wherein the support frame is adapted to generate a data output comprising a pose indicator indicative of a current pose position of the frame.

* * * * *